United States Patent [19]

Barth

[11] Patent Number: 5,330,447
[45] Date of Patent: Jul. 19, 1994

[54] IRRIGATOR FOR COLOSTOMY PATIENTS

[75] Inventor: Reinhardt Barth, Maintal, Fed. Rep. of Germany

[73] Assignee: Pardes Spezialstrumpfe GmbH, Maintal, Fed. Rep. of Germany

[21] Appl. No.: 937,351

[22] Filed: Aug. 27, 1992

[30] Foreign Application Priority Data

Aug. 28, 1991 [DE] Fed. Rep. of Germany ....... 4128420

[51] Int. Cl.⁵ ............................................. A61M 31/00
[52] U.S. Cl. .................................... 604/277; 604/334
[58] Field of Search ............... 128/DIG. 12; 604/118, 604/131, 140–142, 147, 277, 278, 319, 334, 410, 403–405; 131/102.2, 169 R

[56] References Cited

U.S. PATENT DOCUMENTS

| 2,223,566 | 8/1939 | Koch | 604/277 |
|---|---|---|---|
| 2,873,739 | 2/1959 | Whann | 604/118 |
| 3,895,741 | 7/1975 | Nugent | 604/141 |
| 4,090,514 | 5/1978 | Hinck et al. | 604/142 |
| 4,134,404 | 1/1979 | Williams, Jr. | 604/277 |
| 4,270,533 | 6/1981 | Andreas | 604/142 |
| 4,657,160 | 4/1987 | Woods et al. | 604/141 |
| 4,735,613 | 4/1988 | Bellin et al. | 604/118 |
| 4,955,860 | 9/1990 | Ruano | 604/141 |
| 5,053,011 | 10/1991 | Strobel et al. | 604/141 |
| 5,053,012 | 10/1991 | Edwards et al. | 604/118 |
| 5,059,182 | 10/1991 | Laing | 604/141 |
| 5,074,839 | 12/1991 | Chokski et al. | 604/410 |

FOREIGN PATENT DOCUMENTS

| 0385916 | 9/1990 | European Pat. Off. . |
| 2916835 | 4/1970 | Fed. Rep. of Germany . |
| 8303620 | 2/1985 | Fed. Rep. of Germany . |
| 8803818 | 6/1988 | World Int. Prop. O. ......... 604/277 |

*Primary Examiner*—Randall L. Green
*Assistant Examiner*—Rob Clarke
*Attorney, Agent, or Firm*—Robert W. Becker & Associates

[57] ABSTRACT

An irrigator for colostomy patients consists of a bag for receiving a flushing liquid, the bag having a membrane dividing the bag into an air chamber on one side and a closable flushing liquid chamber on the other side. A drainage line is connected to the bag, and a pump is connected to the air chamber is provided for pressurizing the same.

11 Claims, 2 Drawing Sheets

IRRIGATOR FOR COLOSTOMY PATIENTS

BACKGROUND OF THE INVENTION

The present invention relates to an irrigator for colostomy patients comprised of a bag for receiving flushing liquid and a drainage line.

Such an irrigator is used by colostomy patients in order to perform an intestinal flushing or irrigation. With a careful irrigation a secretion-free period of up to 48 hours may be achieved whereby this secretion-free period depends greatly on the remaining length of the patient's intestine and further patient-specific parameters.

The commonly used irrigators are comprised essentially of a bag which at its upper portion is provided with at least one suspending eye. The bag is further provided with a funnel-shaped means so that filling with tap water is possible without difficulties. A drainage line is connected to the lower portion of the bag which widens into a cone and can be closed off with a clamp, for example, a roller clamp. For performing an intestinal flushing the bag is filled with water and suspended from a wall hook so that due to the elevational difference between the bag and the cone a pressure is generated which is sufficient for the intestinal flushing process.

With this known irrigator it is disadvantageous that a suspension device must be provided at a suitable location. This cannot always be ensured, for example, when the colostomy patient is traveling. Improved irrigators are provided with a check valve at the water inlet, however, when the bag is accidentally dropped from the suspension device and is accidentally impacted at the water inlet a failure of the check valve may not be prevented because, on the one hand, it must be freely movable in order to be opened by the inflowing water and, on the other hand, it is incorporated into the essentially very flexible bag.

For eliminating the disadvantages of the actually very flexible and universally employable irrigators, an electric irrigator has been developed which operates according to a somewhat different principle: instead of a bag a water tank is provided. A stable and stiff housing contains the water tank, a controllable pump unit and electronic controls as well as a voltage supply. The electronic controls regulate the output of the pump. In the known device the voltage supply is in the form of accumulators which must be recharged after each flushing process.

This electric irrigator is essentially independent of any location so that a suspension device is not required. Furthermore, the shut-off clamp for the drainage line is eliminated. However, the device is so heavy that it has not been successful in practice because especially when traveling an additional weight load of, for example, more than 1 kilogram is an unbearable load for a colostomy patient without traveling companion. Furthermore, the accumulators of the device are depleted after a one time use. It is possible to recharge the accumulator with a respective recharging device, however, this is an additional load that must be carried by the colostomy patient. Also, in order to be able to recharge the accumulators, the colostomy patient, when traveling is dependent on a respective electrical outlet, with the recharging process commonly requiring about 10 hours. Furthermore, due to the well-known properties of accumulators the recharging process should be initiated immediately after completion of the irrigation which further impairs the traveling flexibility of the colostomy patient.

The operation of such an electric irrigator solely with batteries, respectively, replacement batteries, is not suitable for a plurality of other reasons.

It is therefore an object of the present invention to provide an irrigator of the aforementioned kind which combines a more flexible handling with a higher safety and reliability without requiring additional costs or substantial weight additions.

BRIEF DESCRIPTION OF THE DRAWINGS

This object, and other objects and advantages of the present invention, will appear more clearly from the following specification in conjunction with the accompanying drawing. It is shown in.

SUMMARY OF THE INVENTION

Figure 1:
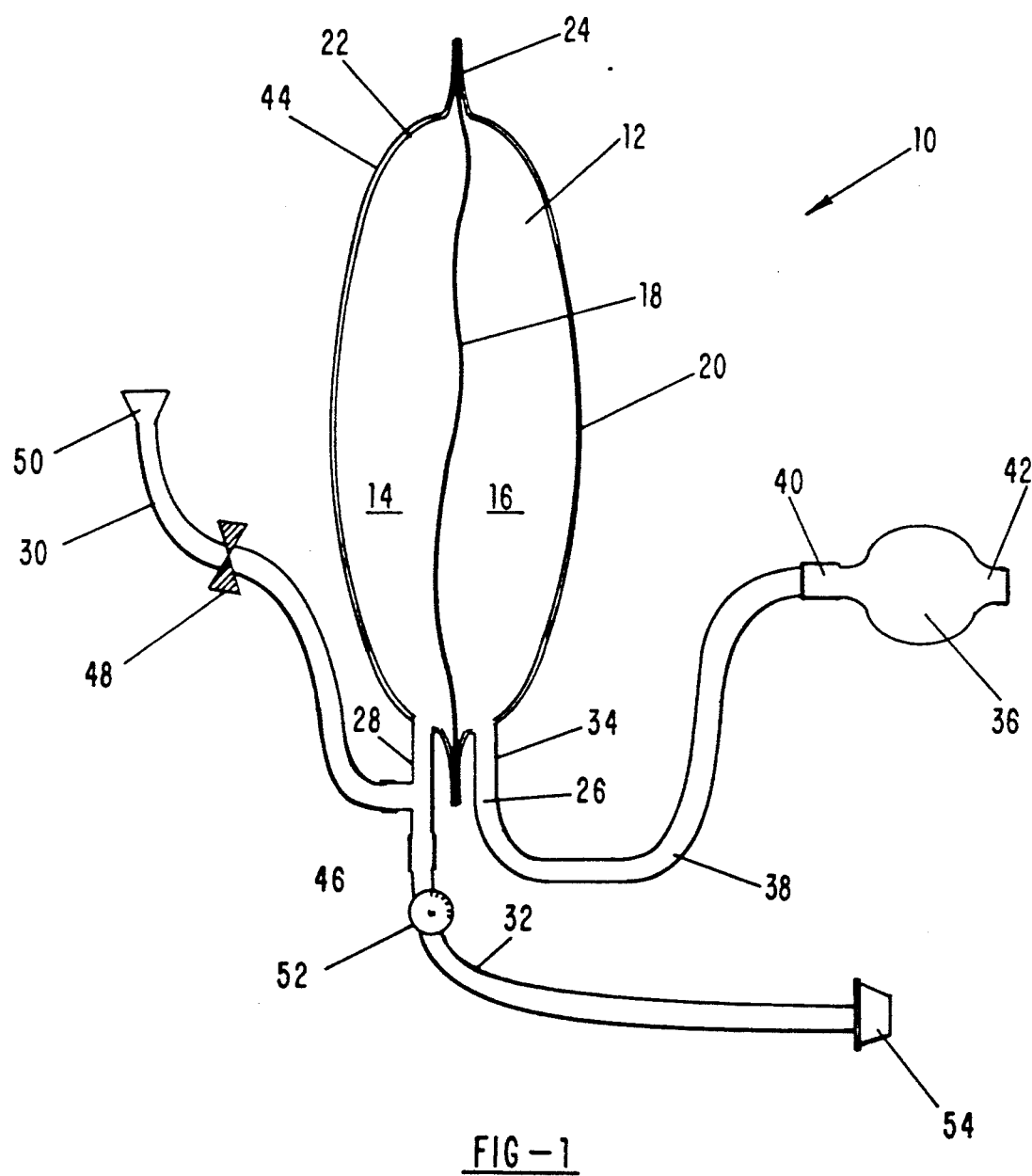
FIG. 1 an inventive irrigator schematically represented in cross-section.

The irrigator of the present invention comprises a bag for receiving a flushing liquid, the bag having a membrane dividing the bag into an air chamber on one side and a closable flushing liquid chamber on the other side; a drainage line connected to the bag; and a pump connected to the air chamber for pressurizing the same. The irrigator further comprises a hose connecting the pump and the sir chamber. Preferably, the pump is a ball-shaped hand pump.

Advantageously, the irrigator further comprises an outlet valve, for reducing the pressure in the air chamber, connected to one of the elements selected from the group consisting of the sir chamber, the hose, and the pump.

In an advantageous embodiment of the present invention, the drainage line further comprises a valve for the flushing liquid. Preferably, the valve is a pressure reducing valve preset to a maximum release pressure, with the release pressure adjustable between zero and said maximum release pressure.

Preferably, the irrigator further comprises an inlet line or inlet hose connected to the flushing liquid chamber the inlet hose having a shut-off valve. Expediently, the inlet hose and the drainage line are both guided into the flushing liquid chamber and are connected to one another, preferably by a T-connector.

Advantageously, the membrane has a first and a second end position, wherein in the first end position a volume of the flushing liquid chamber is at a minimum and a volume of the air chamber is at a maximum and wherein in the second end position the volume of the flushing liquid chamber is at a maximum and the volume of the air chamber is at a minimum. The membrane is movable between the first and the second end position whereby the maximum volumes of the flushing liquid chamber and the air chamber are essentially identical and especially the minimum volumes of the flushing liquid chamber and the air chamber are essentially identical.

The irrigator is preferably made of a flexible, essentially non-elastically stretchable material and has at least one volume-increasing fold on either one of the sides. Preferably, the flexible, essentially non-elastically stretchable material is selected from the group consisting of polyethylene and polyvinyl chloride.

Expediently the bag on the side having the flushing liquid chamber has a filling level indicator and is transparent.

The inventive irrigator has the advantage that it may be used without a suspension device. This means that an intestinal flushing may be performed within a restroom that is not provided with such a suspension device. The weight of the inventive irrigator however corresponds practically to the weight of the commonly used manual irrigators because the additional parts are lightweight and the comparatively large check valve as well as the funnel-shaped water inlet of the known devices are no longer needed, respectively, may be replaced by an inlet hose.

It is furthermore expedient that the fact that the known irrigator bags must have a certain pressure resistance or stability in order to prevent breakage when dropped can be employed for the present invention. This pressure stability is now inventively used to generate a pressure via the inventive membrane which divides the bag into two chambers so that the bag is usable independent of its position. An electric system which is especially dangerous in areas with water supplies can be entirely omitted by providing a small hand pump for generating the required pressure. The pressure generated within the air chamber acts via the membrane in the bag onto the flushing liquid chamber. Due to the elasticity of the air volume a pressure reserve is furthermore provided so that even at the end of the flushing cycle a sufficient pressure is still present.

Especially advantageous in this context is the use of a pressure reducing valve that in a known manner may be inserted as a small and lightweight component into the drainage line. The pressure reducing valve may be preset to a fixedly determined maximum pressure of, for example, 250 mbar which in practice may be reduced to a value of for example 100 mbar. During the entire flushing cycle the desired flushing pressure is present whereby with the aid of the hand pump a pressure of substantially more than 250 mbar may be generated without difficulties.

Since the flushing liquid chamber is closable, the air chamber may be pressurized without regard to its position. Thus, with respect to the known irrigators, a decisive advantage results based on the closibility of the bag, while on the other hand the generation of the required pressure is essentially possible with any desired manual means.

In this context, the use of a manual ball-shaped pump is preferred since on the one hand it strengthens the hand muscles of the patient and thereby contributes to his physical fitness, and on the other hand for its actuation the use of any abdominal muscles is not required.

The inventive irrigator favorably compares in its functionality to the known electric irrigator. Due to its simple design, its reliability is increased and the accessibility for cleaning is substantially improved.

Furthermore, the inventive irrigator is advantageous with respect to its packing volume because the inventive bag is easily folded, and the manual ball-shaped pump is furthermore elastic. Accordingly, the only hard components of the inventive irrigator are the hoses and the pressure reducing valve which is also made of plastic material and which is furthermore very small. The weight of the inventive irrigator is thus only a fraction of the weight of an electric irrigator so that considerable handling advantages result.

The material properties of plastic materials such as polyethylene, polypropylene, and polyvinyl chloride may advantageously be used for the function of the device. The wall thickness of the bag to be used corresponds essentially to the wall thickness of the known irrigator whereby the air chamber may be pressurized to its full extent without causing an overextension of the bag. Accordingly, a slight buffering effect of the elastic air volume as well as of the slightly elastic bag material may be utilized. To further simplify the design the manual ball-shaped pump may be constructed such that the pressure that can be generated with it, including a certain safety reserve, does not exceed the maximum pressure of the air chamber.

From German Gebrauchsmuster 83 03 620.2 a device for infusion or transfusion of bodily fluids is known that operates with a membrane and a ball-shaped pump. This device however is provided with a solid tank so that the desired elasticity effect, which may be further increased by the volume-increasing folds of the bag, cannot be utilized. Since furthermore no drainage line as the one used in the present invention is provided, but the feed as well as the removal of blood takes place via an outlet provided at the cover, there is also no pressure regulating valve provided. Furthermore, this device is designed for transfusion, respectively, reinfusion of blood or plasma replacing substances and is not an irrigator.

Expediently, the inlet line or hose and the drainage line may be connected to the same connector at the flushing fluid chamber whereby it is expedient to provide only one penetration within the wall of the bag and to combine the inlet line and drainage line by a T-connector. This construction has the advantage that only one discontinuity with respect to stiffness exists between the bag and the lines. Thereby, locations of high loads on the materials during folding of the bag are minimized.

According to a further embodiment of the present invention it is suggested to combine the inlet hose and the drainage line. For this purpose, the pressure regulating valve within the drainage line is provided with a bypass which during the drainage cycle is closed and only allows the filling of the bag when the control means is in the filling position. With this embodiment the material expenditure and the weight of the device may be further reduced.

It is understood that the inventive membrane is fused in an airtight and watertight manner to the plastic material of the bag. The flushing liquid chamber may have a maximum volume of, for example, two liters so that a sufficient amount of flushing liquid for a one-step flushing is provided. When the aforementioned combination of inlet hose and drainage line is not utilized, the inlet may be closed off by a simple shut-off valve.

It is especially advantageous when the hose connection for the bag is either a threaded or a plug connection. This allows for a relatively simple cleaning when the irrigator becomes soiled.

DESCRIPTION OF PREFERRED EMBODIMENTS

The present invention will now be described in detail with the aid of a specific embodiment utilizing the only drawing.

The inventive irrigator 10 according to the representation in the only drawing has a bag 12 which is comprised of a flushing liquid chamber 14 and an air chamber 16. The flushing liquid chamber 14 and the air chamber 16 are separated by a membrane 18. The membrane 18 is comprised of the same material as the outer walls 20 and 22 of the bag 12 and is fused to the outer walls 20, 22 about the entire circumference of the bag along the seams 24 and 26 schematically represented in FIG. 1. During fusing of the membrane 18 and the outer walls 20, 22, it must be ensured that the membrane 18 is essentially as bulgy as the two outer walls 20, 22. The bulgy design of the membrane as well as of the two outer walls has the advantage that for the folding of the bag these three layers can be placed onto one another in a fitted manner so that the packing volume is extremely small.

Laterally staggered, however oppositely arranged relative to one another, a connector is provided for each of the chambers 14 and 16. A connector 28 of the flushing liquid chamber 14 is provided for the connection to the hose-like inlet 30 and the drainage line 32. A connector 34 of the air chamber 16 is provided for connecting the pump 36 thereto. In the shown embodiment the pump is in the form of a manual ball-shaped pump. The pump 36, in a known manner, is provided at both ends with a check valve so that a repeated pressing and releasing of the pump volume of the elastic pump 36 results in the desired pumping action. The thus pumped air is introduced via an air hose 38 and connector 34 into the air chamber 16.

In the represented embodiment the pump 36 is connected via a plug connection 40 to the air hose 38. For venting the air chamber 16, for example, when the irrigator 10 must be folded for transporting purposes, or when the flushing fluid chamber 14 must be refilled with water, the plug connection 40 is simply disconnected so that the remaining air within the air chamber 16 is released. By manually applying a slight pressure onto the air chamber 16, the air release may be further facilitated.

According to a further preferred embodiment of the invention it is suggested to provide the pump 36 at its air inlet 42 with a similar plug connection. By simply turning and again inserting the pump 36 into the plug connection 40 of the air hose 38, the remaining air within the air chamber 16 may be pumped out, which is especially expedient for traveling purposes.

As an alternative, a release valve which is not shown in the drawing may be provided anywhere within the area of the air chamber 16, of the air hose 38 and/or the pump 36.

It is furthermore preferable when the connectors 34 and 28 extend essentially within the extension of the membrane 18 close to the seam This is advantageous because the connectors 28 and 34 thus extend favorably within the extension of the folded bag 12 so that they do not bulge especially because they do not laterally overlap.

The flushing fluid chamber 14 in the area of the outer wall 22 is provided with a filling level indicator or markings 44 which indicate the filling level of the flushing liquid chamber 14 when the air chamber is completely empty. It is understood that during the filling of the flushing liquid chamber 14 with water via the inlet hose 30 the plug connection 40 must be separated so that the remaining air may be released from the air chamber 16 unless it has already been pumped out.

The connector 28 is connected via a T-connector 46 to the inlet hose 30 which is provided with a simple shut-off valve 48. For filling the flushing liquid chamber 14 a slightly conical widened portion 50 of the inlet hose 30 is held under a non-represented water faucet. Remaining air within the flushing fluid chamber 14 is of no effect as long as it does not prevent the sufficient filling of the flushing liquid chamber 14. Air may be removed from the chamber 14 by simply turning over the bag 12 so that it can be released via the inlet hose 30.

The drainage line 32 is also connected to the T-connector 46. The drainage line 32 is provided with a pressure reducing valve 52. The pressure reducing valve 52 can be set to positions between zero and a maximum pressure M whereby the maximum pressure M is selected such that it remains below the pressure which would be critical for an intestinal flushing. Between these two end positions the pressure reducing valve 52 is continuously adjustable.

The drainage line 32 is furthermore provided with a known conical portion 54 for connecting the drainage line to the colostomy opening. For filling the flushing liquid chamber 14 the pressure regulating valve 52 is set to zero so that the drainage line 32 is closed. After a sufficient filling level has been reached, the shut-off valve 48 is closed, the pump 36 is inserted with its pressure socket into the plug connection 40, which for example may be in the form of a bayonet plug connection, and the air chamber 16 is pressurized. As soon as the air chamber 16 is completely filled, the cone 54 is applied in the desired manner and the pressure reducing valve 52 is adjusted to the desired pressure with the aid of respective gauge markings. The flushing liquid 14 is then pressed out of the flushing liquid chamber 14 by the pressure that is applied via the membrane 18. After termination of the flushing step the flushing liquid chamber 14 has collapsed to such an extent that the membrane 18 is practically in contact with the outer wall 22 thereby leaving a minimum flushing liquid chamber volume. In contrast, the air chamber 16 still has a high pressure and the air chamber 16 has reached its maximum volume.

For a further filling the plug connection 40 is opened so that the air within the air chamber 16 may be released. For storing the irrigator 10 the remaining air is manually removed from the air chamber 16 so that the outer wall 20 concavely contacts the outer wall 22. This step may be facilitated by removing air via the suction connection of the pump 36. The irrigator 10 is carefully cleaned and may be folded to a small packing volume.

Figure 2:
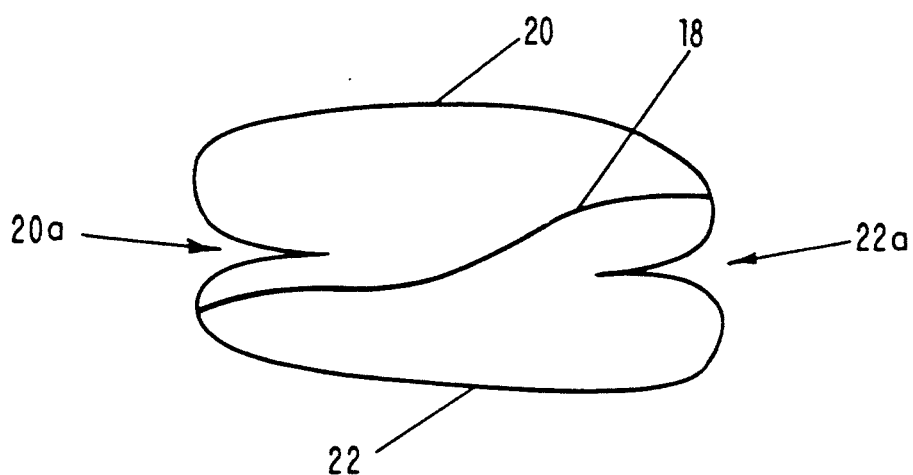
FIG. 2 the irrigator of FIG. 1 with a volume-increasing fold.

It is understood that various embodiments of the aforementioned inventive design are possible without leaving the concept of the present invention. For example, the plug connection 40 may be replaced by a release valve which allows the release of the remaining air. Furthermore, it is possible to connect the inlet hose 30 and the drainage line 32 at opposite ends of the flushing liquid chamber 14. The inlet hose 30 may also be provided with a commonly used funnel in order to facilitate the introduction of water. It is also possible to combine the inlet hose 30 with the drainage line 32 whereby the pressure regulating valve 52 is then bypassed by an integrated check valve in the counter direction which during water introduction opens easily. For this purpose the cone 54 is provided with a respective funnel so that a filling and operation of the irrigator 10 is possible via one single hose. As shown schematically in FIG. 2, the outer walls 20 and 22 of the bag 12 may have volume-increasing folds 20a, 22a.

The present invention is, of course, in no way restricted to the specific disclosure of the specification and drawings, but also encompasses any modifications within the scope of the appended claims.

What I claim is:

1. An irrigator for use by a colostomy patient for intestinal flushing, comprising:
    a bag for receiving a flushing liquid, said bag having a membrane dividing said bag into an air chamber on one side and a closable flushing liquid chamber on the other side;
    a drainage line with a first and a second end and connected with said first end to said bag;
    a connector, connected to said second end of said drainage line, for connecting said drainage line to a colostomy stoma;
    a pump connected to said air chamber for pressurizing same;
    an inlet hose connected to said flushing liquid chamber, said inlet hose having a shut-off valve, wherein said inlet hose and said drainage line are both guided into said flushing liquid chamber and are connected to one another; and
    a T-connector for connecting said inlet hose and said drainage line.

2. An irrigator according to claim 1, further comprising a hose for connecting said pump and said air chamber.

3. An irrigator according to claim 2, wherein said pump is a ball-shaped hand pump.

4. An irrigator according to claim 1, further comprising an outlet valve, for reducing the pressure in said air chamber, connected to one of the elements selected from the group consisting of said air chamber, said hose, and said pump.

5. An irrigator according to claim 1, wherein said drainage line further comprises a valve for the flushing liquid.

6. An irrigator according to claim 5, wherein said valve is a pressure reducing valve preset to a maximum release pressure, with a release pressure adjustable between zero and said maximum release pressure.

7. An irrigator according to claim 1, wherein said membrane has a first and a second end position, wherein in said first end position a volume of said flushing liquid chamber is at a minimum and a volume of said air chamber is at a maximum and wherein in said second end position the volume of said flushing liquid chamber is at a maximum and the volume of said air chamber is at a minimum, said membrane movable between said first and said second end position, with the maximum volumes of said flushing liquid chamber and said air chamber being essentially identical and especially with the minimum volumes of said flushing liquid chamber and said air chamber being essentially identical.

8. An irrigator for use by a colostomy patient for intestinal flushing, comprising:
    a bag for receiving a flushing liquid, said bag having a membrane dividing said bag into an air chamber on one side and a closable flushing liquid chamber on the other side;
    a drainage line with a first and a second end and connected with said first end to said bag;
    a connector, connected to said second end of said drainage line, for connecting said drainage line to a colostomy stoma;
    a pump connected to said air chamber for pressurizing same; and
    wherein said bag is made of a flexible, essentially non-elastically stretchable material and has at least one volume-increasing fold on either one of said sides.

9. An irrigator comprising:
    a bag for receiving a flushing liquid, said bag having a membrane dividing said bag into an air chamber on one side and a closable flushing liquid chamber on the other side;
    a drainage line connected to said bag;
    a pump connected to said air chamber for pressurizing same; and
    wherein said bag is made of a flexible, essentially non-elastically stretchable material and has at least one volume-increasing fold on either one of said sides.

10. An irrigator according to claim 9, wherein said flexible, essentially non-elastically stretchable material is selected from the group consisting of polyethylene and polyvinylchloride.

11. An irrigator according to claim 9, wherein said bag, on said side having said flushing liquid chamber, has a filling level indicator and is transparent.

* * * * *